United States Patent [19]

Terry et al.

[11] Patent Number: 5,562,906
[45] Date of Patent: Oct. 8, 1996

[54] METHOD FOR THE TREATMENT OF VASCULAR DISORDERS

[76] Inventors: James M. Terry, 503 Inwood La., Indian Harbor Beach, Fla. 32937; Richard R. Rathmann, 3950 N. Riverside Dr., Indialantic, Fla. 32903

[21] Appl. No.: 406,268

[22] Filed: Sep. 12, 1989

[51] Int. Cl.$^6$ ................................................. A61K 35/78
[52] U.S. Cl. ................................................. 424/195.1
[58] Field of Search .................... 424/195.1; 514/783, 514/882

[56] References Cited

U.S. PATENT DOCUMENTS

| | | | |
|---|---|---|---|
| 128,169 | 6/1872 | Phillips | 424/195.1 |
| 351,829 | 11/1886 | Davis | 424/195.1 |
| 4,816,481 | 3/1989 | Takasugi | 514/25 |

OTHER PUBLICATIONS

King J. American Dispensatory 8th Ed Cincinnati 1870 pp. 872–873.

Steinmetz E. F. Codex Vegetabilis 1957 Amsterdam #1211, 1212.

Grieve, A Modern Herbal, Dover Publication vol. 1 1931 pp. 70–71.

Krochmal, A Guide to the Medicinal Plants of the U.S. Quadrangle Books no date avail., pp. 238–239.

Merck Index, p. 1012 no date avail.

*Primary Examiner*—Ralph J. Gitomer
*Attorney, Agent, or Firm*—M. K. Silverman

[57] ABSTRACT

Bark or berries of the species Xanthoxylum clavaherculis L and Xanthoxylum americanum Hill, both of the yellow wood tree family, both containing the compound xanthoxylum, are employed for the treatment of hemorrhoids and other membrane and capillary disorders of the veins and arteries. Improved strength and flexibility of the veins, arteries and their constituent structures is obtained.

4 Claims, No Drawings

METHOD FOR THE TREATMENT OF VASCULAR DISORDERS

BACKGROUND OF THE INVENTION

The present invention relates to a new use of the bark of the prickly ash tree which, more particularly, constitutes a method for the treatment of ailments, such as ailments including, without limitation, hemorrhoids and heart disease.

It has, in the prior art, been known that various plants, herbs, bushes, and the like, will yield certain beneficial medicinal effects. More particularly, and in the context of the instant invention, two types of prickly ash trees have been identified. These, in scientific nomenclature, have been termed Xanthoxylum americanum Mill and the Xanthoxylum clava-herculis L. These plant species are, in the American vernacular, known as the northern prickly ash tree and the southern prickly ash tree. The southern prickly ash is also known as the hercules club prickly ash.

The Merck index of pharmacological agents states that the compound known as xanthoxylum is found in the bark of both the northern and southern prickly ash.

The book "A Guide to Medicinal Plants", by Krochmal, published by Quadrangle Books, indicates that the northern prickly ash (Xanthoxylum americanum Mill) is a shrub or small tree growing from five to ten feet in height. The leaves are alternate and compound, with five to eleven leaflets. The stems are petioles and are often prickly. The greenish white flower thereof is small and inconspicuous, and its fruit is reddish, globe-shaped, and aromatic. Krochmal also states that alternate names for the northern prickly ash are american prickly ash, common prickly ash, pellitory bark, toothache bush, toothache tree and yellow wood. Said reference further states that the northern prickly ash is found on river banks and in rich moist woods from New England southward to Alabama, Mississippi, Florida, Georgia, Kentucky, West Virginia and Virginia and westward to North Dakota and Oklahoma.

With respect to its usages, Krochmal states that Indians used the bark as a remedy for toothache, and employed a powder of the bark with water to treat colic, rheumatism, and gonorrhea. Said reference also states that the Indians made the bark into a poultice in combination with bear grease for the purpose of treating sores and ulcers. Krochmal further states that Indians applied the bark to infected wounds to draw out fluids. Also, seeds of the northern prickly ash were employed as a remedy for toothache, and the berries were used in cough syrup to induce the coughing of phlegm. Further, Krochmal states that ripe berries were used in hot water to produce a spray for the treatment of mouth sores.

With regard to the southern prickly ash (the Xanthoxylum clava-herculis L.) Krochmal points out that the southern prickly ash is a shrub or small tree which is five to ten feet in height. The leaves are alternate, compound and with five to eleven leaflets. The stems and petioles are often prickly. The flowers are greenish white, small and inconspicuous. The fruit is a reddish globular to elliptic aromatic capsule, with prickles.

Alternate names for the southern prickly ash are the hercules club, pillenterry, sea ash, scrubby prickly ash, string-a-tong, toothache tree, wait-a-bit and wild orange. Krochmal states that the southern prickly ash is found in sand hills, thickets, dry woods, coastal areas, river banks, and sand dunes. Geographically, it is found in Southern Virginia, Kentucky, West Virginia, Louisiana, Arkansas, Alabama, Mississippi, Florida and Oklahoma.

Krochmal also notes that the southern prickly ash was used by the Indians for a wide range of ailments. More particularly, a mixture of the bark with water was used for the treatment of gonorrhea and the bark itself was used as a treatment for toothache. Roots of the southern prickly ash boiled in water were used to induce perspiration. Krochmal further indicates that both Indians and early settlers mixed the inner bark of the southern prickly ash with bear grease and applied it as a poultices to treat ulcers. Also, ripe berries were boiled in hot water to make a spray and blown onto the chest and throat as a treatment for chest ailments. Further, the bark was used for inflammation of the throat.

In addition, the inner bark of the southern prickly ash was boiled in water to produce a lotion for the treatment of various itches. The berries of the prickly ash were considered a tonic, a stimulant, an anti-rheumatic, and effective in the relief of gas, colic, and muscle spasms.

The Merck index indicates that the constituents of xanthoxylum (the active ingredient in prickly ash) include xanthoxylin-N, acrid volatile oil, resin, and tannin.

Volume I of the work entitled a "Hodem Herbal", by Grieve, published by Dover Books, points out that the prickly ash species is a member of a larger botanical family known as the Yellow Wood (Rutaceae) family, all of which possess aromatic and pungent properties. Grieve points out that both the root bark and the berries are used medicinally, and have achieved some official recognition by the mention of the bark and berries thereof in the U.S. Pharmacopoeia. Grieve indicates that the southern prickly ash is believed to be the more medically active of the two species. Further, Grieve states that although the two species are not identical, the respective barks are very similar in terms of the active constituent, namely, xanthoxylum. Also, Grieve indicates that both barks contain small amounts of volatile oil, fat, sugar, gum, acrid, resin, and a bitter alkaloid, believed to be berberine, as well as the above mentioned xanthoxylin which is a colorless, tasteless, crystalline substance which appears in slightly different forms in the bark of the respective species. Grieve further states that the bark of both species yields twelve per cent or more of xanthoxylin. Grieve further states that the northern prickly ash bark exists in commerce and is sold as curved or quilt fragments about $\frac{1}{24}$ of one inch (about one millimeter) thick and that the bark of the southern prickly ash is generally sold in $\frac{1}{12}$ inch thickness (about two millimeters).

With respect to its medicinal action and usages, Grieve states that the prickly ash has been recommended in the U.S. for chronic rheumatism, typhoid, skin disease and impurity of the blood, and is administered either in the form of a fluid or in dosages of 10 grains (650 milligrams) to 0.5 drams (885 milligrams) in the powdered form, taken three times a day. Grieve goes on to state that the powdered bark forms an excellent application to indolent ulcers and old wounds for cleaning stimulating, drying up and healing such wounds, and that the pulverized bark is used for infections and nervous headaches.

Finally, Grieve states that the berries of the prickly ash are considered even more active that the bark, the berries being carminative and antispasmodic, and are used as an aspirin and for dyspepsia indigestion.

By virtue of the above, it may be appreciated that the bark and berries of species of the prickly ash have been employed in a number of medical applications. However, none of these applications have been concerned with ailments of the vascular system and, more particularly, no use of products of the prickly ash tree has occurred in connection with the treatment of hemorrhoids or cardiovascular disorders. Accordingly the instant invention may be viewed as a new use of a known composition of matter.

SUMMARY OF THE INVENTION

The present invention relates to a method for the treatment of vascular ailments consisting of the periodic use of xanthoxylum in a prescribed dosage. A xanthoxylum compound may be extracted from the bark or berries of species of the prickly ash tree of the yellow wood family for the treatment of vascular ailments including hemorrhoids and rectal irritation, and for the treatment of cardiovascular disorders.

It is accordingly an object of the present invention to provide a convenient and effective method for the treatment of dilation of the veins in swollen tissue situated near the anal sphincter, such condition commonly known as hemorrhoids.

It is another object of the present invention to provide a method for rendering venous tissue stronger and more supple.

It is a further object of the present invention to provide a new use for products of the prickly ash tree and, particularly, use in medicinal areas beneficial to the vascular and cardiovascular system.

The above and yet other objects and advantages of the present invention will become apparent in the hereinafter set forth Detailed Description of the Invention, and Claims appended herewith.

DETAILED DESCRIPTION OF THE INVENTION

The present invention relates to a new use of the bark and/or berries of the Xanthoxylum clava-herculis L. commonly known as the southern prickly ash. The invention further relates to a new use for the Xanthoxylum americanum Hill, commonly known as the northern prickly ash or american prickly ash.

The preferred embodiment relates to the bark of the Xanthoxylum clava- herculis L. in which the bark of the Xanthoxylum clava herculls L. is chewed about three times a day for a period of about three weeks. The bark is preferably chewed in the form of slivers having dimensions of approximately 2.5 centimeters by 2.0 centimeters by 0.5 centimeters and weighing about 2 grams.

Testing of the above use of the bark of Xanthoxylum clava-herculis L. on approximately two hundred people in Florida has indicated that substantial relief from hemorrhoids and rectal irritation is achieved. Based upon medical examination of many of the treated individuals, it is believed that the active ingredient of the Xanthoxylum clava-herulis L, that is, the organic compound known as xanthoxylum, operates to strengthen the venous cellular structure and, more particularly, operates to improve the capillary integrity of the veins and arteries. As such, it is believed that many types of vascular disorders can be addressed by variations of the above method. That is, usage of the bark and other products, such as the berries, of the Xanthoxylum clava-herculis L. and allied yellow wood genii such as the Xanthoxylum americanum Hill, can be advantageously employed in the treatment of a broad spectrum of vascular illnesses which involve the atrophication or hardening of the veins and/or arteries. As such, research is currently in process to study potentially beneficial properties of xanthoxylum in connection with cardiovascular disorders.

In an alternative form of use of the bark of Xanthoxylum clava-herculis L, the bark may be boiled to extract therefrom the xanthoxylum compound. This extract may then be combined with a gum which in turn may be provided with an appropriate flavoring.

The xanthoxylum extract comprises about twelve per cent by weight of the bark from which the extract is taken. Accordingly, a 2 gram silver of bark will yield an extract of 24 gram, or 240 milligrams (4 grains) for the above recommended three times daily dosage of xanthoxylum. As such, the preferred daily dosage, based upon "chewing" the bark, or a gum of the extract, three times a day, is that of about 720 milligrams or 11 grains a day. As above noted, it is believed that both species of the xanthoxylum tree, namely, Xanthoxylum americanum Mill and Xanthoxylum clavaherculis L. can be advantageously employed for the purpose of strengthening capillary structure and contributing to the flexibility of the membranes associated therewith. As such, the instant new use of xanthoxylum departs from that of the prior art in that the essential focus of known herbal use of xanthoxylum has been limited to the treatment of dermatological, neurological and gastro-intestinal disorders. As such, the prior art evidences no concern or awareness of the potential of the xanthoxylum compound in connection with venous and arterial disorders including, particularly, the venous disorder of the anus, commonly known as hemorrhoids.

Accordingly, while there has been shown and described the preferred embodiment of the instant invention, it is to be appreciated that the invention may be embodied otherwise than is herein specifically described and that, within said embodiment, certain changes may be made without departing from the underlying principles of this invention within the scope of the Claims appended herewith.

Having thus described our invention, what we claim as new, useful and non-obvious and, accordingly, secure by Letters Patent of the U.S. is:

1. A method for the treatment of hemorrhoids for use by one in need of such treatment consisting the step of administering about 240 milligrams, about three times a day, xanthoxylum, xanthoxylum derived from xanthoxylum clava herculis L. for the duration of said treatment of hemorrhoids.

2. The method as recited in claim 1, in which said xanthoxylum is ingested by chewing upon slivers of bark of the Xanthoxylum clava herculis L. species of trees, such slivers of bark having a weight of about 2 grams each, and repeating such chewing three times per day.

3. The method as recited in claim 1, in which the administration of Xanthoxylum said comprises the form of chewing upon berries of the xanthoxylum clava herculis L. species of trees, the daily does of said xanthoxylum in berries so ingested being about 720 milligrams.

4. The method as recited in claim 1, further wherein the treatment lasts about fourteen days.

* * * * *